United States Patent [19]
Hudson et al.

[11] Patent Number: 5,994,102
[45] Date of Patent: Nov. 30, 1999

[54] POLYNUCLEOTIDES ENCODING PROSTATIC GROWTH FACTOR AND PROCESS FOR PRODUCING PROSTATIC GROWTH FACTOR POLYPEPTIDES

[75] Inventors: Peter L. Hudson, Germantown; Craig A. Rosen, Laytonsville; Wei Wu He, Columbia, all of Md.

[73] Assignee: Human Genome Sciences, Inc., Rockville, Md.

[21] Appl. No.: 08/411,607

[22] PCT Filed: Dec. 15, 1994

[86] PCT No.: PCT/US94/14578

§ 371 Date: Oct. 2, 1995

§ 102(e) Date: Oct. 2, 1995

[87] PCT Pub. No.: WO96/18730

PCT Pub. Date: Jun. 20, 1996

[51] Int. Cl.[6] .......................... C12N 15/12; C12N 15/63; C12N 1/21; C07K 14/475
[52] U.S. Cl. .................. 435/69.4; 435/320.1; 435/325; 435/243; 536/23.1; 536/23.4; 536/23.51; 530/399; 530/854
[58] Field of Search ................. 435/69.4, 69.1, 435/240.1, 320.1; 536/23.1, 23.51; 530/399, 350

[56] References Cited

U.S. PATENT DOCUMENTS

| | | | |
|---|---|---|---|
| 4,931,548 | 6/1990 | Lucas et al. | 530/399 |
| 5,168,051 | 12/1992 | Derrynck et al. | 435/69.4 |
| 5,221,620 | 6/1993 | Purchio et al. | 435/69.7 |
| 5,223,408 | 6/1993 | Goeddel et al. | 435/69.3 |

FOREIGN PATENT DOCUMENTS

| | | |
|---|---|---|
| 07250688 | 10/1995 | Japan . |
| 7-250688 | 10/1995 | Japan . |
| 7-258293 | 10/1995 | Japan . |
| 97/00958 | 1/1997 | WIPO . |
| 97/36926 | 10/1997 | WIPO . |
| 98/11224 | 3/1998 | WIPO . |

OTHER PUBLICATIONS

George et al. Macromolecular Sequencing & Synth. pp. 127–149, 1988.

Anscher et al., *The New England Journal of Medicine,* Jun. 3, 1993, vol. 328, No. 22, pp. 1592–1598.

Lin et al., *Cell,* Feb. 21, 1992, vol. 68, pp. 775–785.

*Primary Examiner*—John Ulm
*Assistant Examiner*—Christine Saoud
*Attorney, Agent, or Firm*—Kenley K. Hoover

[57] ABSTRACT

The present invention relates to polynucleotides encoding human PGF polypeptides, variant polynucleotides encoding analog polypeptides, and variant polynucleotides useful as probes for polynucleotides encoding human PGF polypeptides. Also provided is a procedure for producing such polypeptides by recombinant techniques.

29 Claims, 2 Drawing Sheets

```
gcacacgagg caacctgcac agccatgccc gggcaagaac tcaggacgct gaatggctct   60 cag atg ctc ctg gtg ttg ctg gtg ctc tcg tgg ctg ccg cat ggg ggc   108
    Met Leu Leu Val Leu Leu Val Leu Ser Trp Leu Pro His Gly Gly gcc ctg tct ctg gcc gag gcg agc cgc gca agt ttc ccg gga ccc tca   156
Ala Leu Ser Leu Ala Glu Ala Ser Arg Ala Ser Phe Pro Gly Pro Ser gag ttg cac tcc gaa gac tcc aga ttc cga gag ttg cgg aaa cgc tac   204
Glu Leu His Ser Glu Asp Ser Arg Phe Arg Glu Leu Arg Lys Arg Tyr gag gac ctg cta acc agg ctg cgg gcc aac cag agc tgg gaa gat tcg   252
Glu Asp Leu Leu Thr Arg Leu Arg Ala Asn Gln Ser Trp Glu Asp Ser aac acc gac ctc gtc ccg gcc cct gca gtc cgg ata ctc acg cca gaa   300
Asn Thr Asp Leu Val Pro Ala Pro Ala Val Arg Ile Leu Thr Pro Glu gtg cgg ctg gga tcc ggc ggc cac ctg cac ctg cgt atc tct cgg gcc   348
Val Arg Leu Gly Ser Gly Gly His Leu His Leu Arg Ile Ser Arg Ala gcc ctt ccc gag ggg ctc ccc gag gcc tcc cgc ctt cac cgg gct ctg   396
Ala Leu Pro Glu Gly Leu Pro Glu Ala Ser Arg Leu His Arg Ala Leu ttc cgg ctg tcc ccg acg gcg tca agg tcg tgg gac gtg aca cga ccg   444
Phe Arg Leu Ser Pro Thr Ala Ser Arg Ser Trp Asp Val Thr Arg Pro ctg cgg cgt cag ctc agc ctt gca aga ccc cag gcg ccc gcg ctg cac   492
Leu Arg Arg Gln Leu Ser Leu Ala Arg Pro Gln Ala Pro Ala Leu His ctg cga ctg tcg ccg ccg ccg tcg cag tcg gac caa ctg ctg gca gaa   540
Leu Arg Leu Ser Pro Pro Pro Ser Gln Ser Asp Gln Leu Leu Ala Glu tct tcg tcc gca cgg ccc cag ctg gag ttg cac ttg cgg ccg caa gcc   588
Ser Ser Ser Ala Arg Pro Gln Leu Glu Leu His Leu Arg Pro Gln Ala gcc agg ggg cgc cgc aga gcg cgt gcg cgc aac ggg gac cac tgt ccg   636
Ala Arg Gly Arg Arg Arg Ala Arg Ala Arg Asn Gly Asp His Cys Pro ctc ggg ccc ggg cgt tgc tgc cgt ctg cac acg gtc cgc gcg tcg ctg   684
Leu Gly Pro Gly Arg Cys Cys Arg Leu His Thr Val Arg Ala Ser Leu gaa gac ctg ggc tgg gcc gat tgg gtg ctg tcg cca cgg gag gtg caa   732
Glu Asp Leu Gly Trp Ala Asp Trp Val Leu Ser Pro Arg Glu Val Gln gtg acc atg tgc atc ggc gcg tgc ccg agc cag ttc cgg gcg gca aac   780
Val Thr Met Cys Ile Gly Ala Cys Pro Ser Gln Phe Arg Ala Ala Asn atg cac gcg cag atc aag acg agc ctg cac cgc ctg aag ccc gac acg   828
Met His Ala Gln Ile Lys Thr Ser Leu His Arg Leu Lys Pro Asp Thr gtg cca gcg ccc tgc tgc gtg ccc gcc agc tac aat ccc atg gtg ctc   876
Val Pro Ala Pro Cys Cys Val Pro Ala Ser Tyr Asn Pro Met Val Leu att caa aag acc gac acc ggg gtg tcg ctc cag acc tat gat gac ttg   924
Ile Gln Lys Thr Asp Thr Gly Val Ser Leu Gln Thr Tyr Asp Asp Leu tta gcc aaa gac tgc cac tgc ata tga gca gtc ctg gtc ctt cca ctg   972
Leu Ala Lys Asp Cys His Cys Ile tgc acc tgc gcg ggg gac ggg acc tca gtt gtc ctg ccc tgtggaatgc   1021 gct                                                                1024
```

FIG. 1

```
  1  MLLVL--------VLSWLP-----HGGALSLAEASRAS  PGF
  1  MHVRSLRAAAPHSFVALWAPLFLLRSALADFSLDNEVHSS  OP-1
  1  M---------------VWLRLWAFLHILAIVTLDPELKR-  Vg1

27  F-------PGPSELHSE-------------------  PGF
 41  FIHRRLRSQERREMQREILSILGLPHRPRPHLQGKHNSAP  OP-1
 25  --------REEL---FLRSLGFSSKPNP---VSPPPVP  Vg1

37  ---------------------------------------  PGF
 81  MFMLDLYNAMAVEEGGGPGGQGFSYPYKAVFSTQGPPLAS  OP-1
 49  SILWRIFNQRM---GSSIQKKKPDLCFVEEFNVPGSVI--  Vg1

37  --DSRFRE---LRKRYEDLLTR---LRANQSWED------  PGF
121  LQDSHFLTDADMVMSFVNLVEHDKEFFHPRYHHREFRFDL  OP-1
 84  ---RVFPDGRFIIPYSD------DIHPTQCLEKRLFFNI  Vg1

63  ---SNTDLVPAPAVRI---LTPEVRLGSGGHLHL-RISRA  PGF
161  SKIPEGEAVTAAEFRIYKDYIRERFDNETFRISVYQVLQE  OP-1
115  SAIEKEERVTMGSG---IEVQPEHLLRKGIDLRLYRTLQI  Vg1

96  ALPEGLPEASRLHRVL---FRLSPTA---------SRSW  PGF
201  HL----GRESDLF-LLDSRTLWASEEGWLVFDITATSNHW  OP-1
152  TL-KGMGRSKTSRKLLVAQTFRLLHKS-LFFNLTEICQSW  Vg1

123  DVTRPLRRQLSLA------RPQAPALHRLSPPPSQSDQL  PGF
236  VVNPRHNLGLQLSVETLDGQSINPKLAGLIGRHGPQNKQP  OP-1
190  Q-DPLKNLGLVLEI------FPKKESSWMSTANDECKDI  Vg1

157  LAESSSARPQLELH-LRPQAARGRRARARN---------  PGF
276  FMVAFFKATEVHFRSIRSTGSKQRSQNRSKTPKNQEALRM  OP-1
222  QTFLYTSLLTVTLNPLRC------KRPRRKRSYSKLPF  Vg1

187  ---GDHCPLGPGRCCRLHTVRASLEDLGWADWVLSPREVQ  PGF
316  ANVAENSSSDQRQACKKHELYVSFRDLGWQDWIIAPEGYA  OP-1
254  TA---------SNICKKRHLYVEFKDVGWQNWVIAPQGYM  Vg1

224  VTMCIGACP---SQFRAANMHAQIKTSLHRLKPDTVPAPC  PGF
356  AYYCEGECAFPLNSYMNATNHAIVQTLVHFINPETVPKPC  OP-1
285  ANYCYGECPYPLTEILNGSNHAILQTLVHSIEPEDIPLPC  Vg1

261  CVPASYNPM-VLIQKTDTGVSFQTYDDLLAKDCHCI  PGF
396  CAPTQLNAISVLYFDDSSNVILKKYRNMVVRACGCH  OP-1
325  CVPTKMSPISMLFYDNNDNVVLRHYENMAVDECGCR  Vg1
```

FIG.2

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 1024 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 64..948

(xi) SEQUENCE DESCRIPTION: SEQ ID NO:1:

```
GCACACGAGG CAACCTGCAC AGCCATGCCC GGGCAAGAAC TCAGGACGCT GAATGGCTCT          60

CAG ATG CTC CTG GTG TTG CTG GTG CTC TCG TGG CTG CCG CAT GGG GGC          108
    Met Leu Leu Val Leu Leu Val Leu Ser Trp Leu Pro His Gly Gly
     1               5                  10                  15

GCC CTG TCT CTG GCC GAG GCG AGC CGC GCA AGT TTC CCG GGA CCC TCA          156
Ala Leu Ser Leu Ala Glu Ala Ser Arg Ala Ser Phe Pro Gly Pro Ser
                 20                  25                  30

GAG TTG CAC TCC GAA GAC TCC AGA TTC CGA GAG TTG CGG AAA CGC TAC          204
Glu Leu His Ser Glu Asp Ser Arg Phe Arg Glu Leu Arg Lys Arg Tyr
             35                  40                  45

GAG GAC CTG CTA ACC AGG CTG CGG GCC AAC CAG AGC TGG GAA GAT TCG          252
Glu Asp Leu Leu Thr Arg Leu Arg Ala Asn Gln Ser Trp Glu Asp Ser
         50                  55                  60

AAC ACC GAC CTC GTC CCG GCC CCT GCA GTC CGG ATA CTC ACG CCA GAA          300
Asn Thr Asp Leu Val Pro Ala Pro Ala Val Arg Ile Leu Thr Pro Glu
 65                  70                  75

GTG CGG CTG GGA TCC GGC GGC CAC CTG CAC CTG CGT ATC TCT CGG GCC          348
Val Arg Leu Gly Ser Gly Gly His Leu His Leu Arg Ile Ser Arg Ala
 80                  85                  90                  95

GCC CTT CCC GAG GGG CTC CCC GAG GCC TCC CGC CTT CAC CGG GCT CTG          396
Ala Leu Pro Glu Gly Leu Pro Glu Ala Ser Arg Leu His Arg Ala Leu
                100                 105                 110

TTC CGG CTG TCC CCG ACG GCG TCA AGG TCG TGG GAC GTG ACA CGA CCG          444
Phe Arg Leu Ser Pro Thr Ala Ser Arg Ser Trp Asp Val Thr Arg Pro
            115                 120                 125
```

```
CTG CGG CGT CAG CTC AGC CTT GCA AGA CCC CAG GCG CCC GCG CTG CAC      492
Leu Arg Arg Gln Leu Ser Leu Ala Arg Pro Gln Ala Pro Ala Leu His
            130                 135                 140

CTG CGA CTG TCG CCG CCG CCG TCG CAG TCG GAC CAA CTG CTG GCA GAA      540
Leu Arg Leu Ser Pro Pro Pro Ser Gln Ser Asp Gln Leu Leu Ala Glu
        145                 150                 155

TCT TCG TCC GCA CGG CCC CAG CTG GAG TTG CAC TTG CGG CCG CAA GCC      588
Ser Ser Ser Ala Arg Pro Gln Leu Glu Leu His Leu Arg Pro Gln Ala
160                 165                 170                 175

GCC AGG GGG CGC CGC AGA GCG CGT GCG CGC AAC GGG GAC CAC TGT CCG      636
Ala Arg Gly Arg Arg Arg Ala Arg Ala Arg Asn Gly Asp His Cys Pro
                180                 185                 190

CTC GGG CCC GGG CGT TGC TGC CGT CTG CAC ACG GTC CGC GCG TCG CTG      684
Leu Gly Pro Gly Arg Cys Cys Arg Leu His Thr Val Arg Ala Ser Leu
            195                 200                 205

GAA GAC CTG GGC TGG GCC GAT TGG GTG CTG TCG CCA CGG GAG GTG CAA      732
Glu Asp Leu Gly Trp Ala Asp Trp Val Leu Ser Pro Arg Glu Val Gln
        210                 215                 220

GTG ACC ATG TGC ATC GGC GCG TGC CCG AGC CAG TTC CGG GCG GCA AAC      780
Val Thr Met Cys Ile Gly Ala Cys Pro Ser Gln Phe Arg Ala Ala Asn
225                 230                 235

ATG CAC GCG CAG ATC AAG ACG AGC CTG CAC CGC CTG AAG CCC GAC ACG      828
Met His Ala Gln Ile Lys Thr Ser Leu His Arg Leu Lys Pro Asp Thr
240                 245                 250                 255

GTG CCA GCG CCC TGC TGC GTG CCC GCC AGC TAC AAT CCC ATG GTG CTC      876
Val Pro Ala Pro Cys Cys Val Pro Ala Ser Tyr Asn Pro Met Val Leu
            260                 265                 270

ATT CAA AAG ACC GAC ACC GGG GTG TCG TTC CAA ACC TAT GAT GAC TTG      924
Ile Gln Lys Thr Asp Thr Gly Val Ser Phe Gln Thr Tyr Asp Asp Leu
        275                 280                 285

TTA GCC AAA GAC TGC CAC TGC ATA TGAGCAGTCC TGGTCCTTCC ACTGTGCACC     978
Leu Ala Lys Asp Cys His Cys Ile
290                 295

TGCGCGGGGG ACGGGACCTC AGTTGTCCTG CCCTGTGGAA TGCGCT                  1024

(2) INFORMATION FOR SEQ ID NO:2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:2:

Met Leu Leu Val Leu Leu Val Leu Ser Trp Leu Pro His Gly Gly Ala
 1               5                  10                  15

Leu Ser Leu Ala Glu Ala Ser Arg Ala Ser Phe Pro Gly Pro Ser Glu
            20                  25                  30

Leu His Ser Glu Asp Ser Arg Phe Arg Glu Leu Arg Lys Arg Tyr Glu
        35                  40                  45

Asp Leu Leu Thr Arg Leu Arg Ala Asn Gln Ser Trp Glu Asp Ser Asn
    50                  55                  60

Thr Asp Leu Val Pro Ala Pro Ala Val Arg Ile Leu Thr Pro Glu Val
65                  70                  75                  80

Arg Leu Gly Ser Gly Gly His Leu His Leu Arg Ile Ser Arg Ala Ala
                85                  90                  95

Leu Pro Glu Gly Leu Pro Glu Ala Ser Arg Leu His Arg Ala Leu Phe
            100                 105                 110
```

```
Arg Leu Ser Pro Thr Ala Ser Arg Ser Trp Asp Val Thr Arg Pro Leu
        115                 120                 125

Arg Arg Gln Leu Ser Leu Ala Arg Pro Gln Ala Pro Ala Leu His Leu
130                 135                 140

Arg Leu Ser Pro Pro Pro Ser Gln Ser Asp Gln Leu Leu Ala Glu Ser
145                 150                 155                 160

Ser Ser Ala Arg Pro Gln Leu Glu Leu His Leu Arg Pro Gln Ala Ala
                165                 170                 175

Arg Gly Arg Arg Ala Arg Ala Arg Asn Gly Asp His Cys Pro Leu
                180                 185                 190

Gly Pro Gly Arg Cys Cys Arg Leu His Thr Val Arg Ala Ser Leu Glu
            195                 200                 205

Asp Leu Gly Trp Ala Asp Trp Val Leu Ser Pro Arg Glu Val Gln Val
            210                 215                 220

Thr Met Cys Ile Gly Ala Cys Pro Ser Gln Phe Arg Ala Ala Asn Met
225                 230                 235                 240

His Ala Gln Ile Lys Thr Ser Leu His Arg Leu Lys Pro Asp Thr Val
                245                 250                 255

Pro Ala Pro Cys Cys Val Pro Ala Ser Tyr Asn Pro Met Val Leu Ile
                260                 265                 270

Gln Lys Thr Asp Thr Gly Val Ser Phe Gln Thr Tyr Asp Asp Leu Leu
            275                 280                 285

Ala Lys Asp Cys His Cys Ile
290                 295

(2) INFORMATION FOR SEQ ID NO:3:

(i) SEQUENCE CHARACTERISTICS:
        (A) LENGTH: 432 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Glu Ser His Phe Leu
        115                 120                 125

Thr Asp Ala Asp Met Val Met Ser Phe Val Asn Leu Val Glu His Asp
130                 135                 140

Lys Glu Phe Phe His Pro Arg Tyr His His Arg Glu Phe Arg Phe Asp
145                 150                 155                 160

Leu Ser Lys Ile Pro Glu Gly Glu Ala Val Thr Ala Ala Glu Phe Arg
```

```
                    165                 170                 175
Ile Tyr Lys Asp Tyr Ile Arg Glu Arg Phe Asp Asn Glu Thr Phe Arg
            180                 185                 190
Ile Ser Val Tyr Gln Val Leu Gln Glu His Leu Gly Arg Glu Ser Asp
            195                 200                 205
Leu Phe Leu Leu Asp Ser Arg Thr Leu Trp Ala Ser Glu Glu Gly Trp
            210                 215                 220
Leu Val Phe Asp Ile Thr Ala Thr Ser Asn His Trp Val Val Asn Pro
225                 230                 235                 240
Arg His Asn Leu Gly Leu Gln Leu Ser Val Glu Thr Leu Asp Gly Gln
                245                 250                 255
Ser Ile Asn Pro Lys Leu Ala Gly Leu Ile Gly Arg His Gly Pro Gln
                260                 265                 270
Asn Lys Gln Pro Phe Met Val Ala Phe Phe Lys Ala Thr Glu Val His
            275                 280                 285
Phe Arg Ser Ile Arg Ser Thr Gly Ser Lys Gln Arg Ser Gln Asn Arg
            290                 295                 300
Ser Lys Thr Pro Lys Asn Gln Glu Ala Leu Arg Met Ala Asn Val Ala
305                 310                 315                 320
Glu Asn Ser Ser Ser Asp Gln Arg Gln Ala Cys Lys Lys His Glu Leu
                325                 330                 335
Tyr Val Ser Phe Arg Asp Leu Gly Trp Gln Asp Trp Ile Ile Ala Pro
            340                 345                 350
Glu Gly Tyr Ala Ala Tyr Tyr Cys Glu Gly Glu Cys Ala Phe Pro Leu
            355                 360                 365
Asn Ser Tyr Met Asn Ala Thr Asn His Ala Ile Val Gln Thr Leu Val
            370                 375                 380
His Phe Ile Asn Pro Glu Thr Val Pro Lys Pro Cys Cys Ala Pro Thr
385                 390                 395                 400
Gln Leu Asn Ala Ile Ser Val Leu Tyr Phe Asp Asp Ser Ser Asn Val
                405                 410                 415
Ile Leu Lys Lys Tyr Arg Asn Met Val Val Arg Ala Cys Gly Cys His
                420                 425                 430

(2) INFORMATION FOR SEQ ID NO:4:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Val Trp Leu Arg Leu Trp Ala Phe Leu His Ile Leu Ala Ile Val
1               5                   10                  15
Thr Leu Asp Pro Glu Leu Lys Arg Arg Glu Glu Leu Phe Leu Arg Ser
            20                  25                  30
Leu Gly Phe Ser Ser Lys Pro Asn Pro Val Ser Pro Pro Val Pro
            35                  40                  45
Ser Ile Leu Trp Arg Ile Phe Asn Gln Arg Met Gly Ser Ser Ile Gln
50                  55                  60
Lys Lys Lys Pro Asp Leu Cys Phe Val Glu Glu Phe Asn Val Pro Gly
65                  70                  75                  80
Ser Val Ile Arg Val Phe Pro Asp Gln Gly Arg Phe Ile Ile Pro Tyr
                85                  90                  95
```

```
Ser Asp Asp Ile His Pro Thr Gln Cys Leu Glu Lys Arg Leu Phe Phe
            100                 105                 110

Asn Ile Ser Ala Ile Glu Lys Glu Glu Arg Val Thr Met Gly Ser Gly
            115                 120                 125

Ile Glu Val Gln Pro Glu His Leu Leu Arg Lys Gly Ile Asp Leu Arg
            130                 135                 140

Leu Tyr Arg Thr Leu Gln Ile Thr Leu Lys Gly Met Gly Arg Ser Lys
145                 150                 155                 160

Thr Ser Arg Lys Leu Leu Val Ala Gln Thr Phe Arg Leu Leu His Lys
                165                 170                 175

Ser Leu Phe Phe Asn Leu Thr Glu Ile Cys Gln Ser Trp Gln Asp Pro
            180                 185                 190

Leu Lys Asn Leu Gly Leu Val Leu Glu Ile Phe Pro Lys Lys Glu Ser
            195                 200                 205

Ser Trp Met Ser Thr Ala Asn Asp Glu Cys Lys Asp Ile Gln Thr Phe
            210                 215                 220

Leu Tyr Thr Ser Leu Leu Thr Val Thr Leu Asn Pro Leu Arg Cys Lys
225                 230                 235                 240

Arg Pro Arg Arg Lys Arg Ser Tyr Ser Lys Leu Pro Phe Thr Ala Ser
                245                 250                 255

Asn Ile Cys Lys Lys Arg His Leu Tyr Val Glu Phe Lys Asp Val Gly
            260                 265                 270

Trp Gln Asn Trp Val Ile Ala Pro Gln Gly Tyr Met Ala Asn Tyr Cys
            275                 280                 285

Tyr Gly Glu Cys Pro Tyr Pro Leu Thr Glu Ile Leu Asn Gly Ser Asn
            290                 295                 300

His Ala Ile Leu Gln Thr Leu Val His Ser Ile Glu Pro Glu Asp Ile
305                 310                 315                 320

Pro Leu Pro Cys Cys Val Pro Thr Lys Met Ser Pro Ile Ser Met Leu
                325                 330                 335

Phe Tyr Asp Asn Asn Asp Asn Val Val Leu Arg His Tyr Glu Asn Met
            340                 345                 350

Ala Val Asp Glu Cys Gly Cys Arg
            355                 360

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGCGCGAAGC TTATGCTCCT GGTGTTGCTG GTG                                33

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:
```

```
GCGCGCTCTA GATCATATGC AGTGGCAGTC TTT                                    33

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCGCAGATCT GCCACCATGC TCCTGGTGTT GCTGGTGCTG                             40

(2) INFORMATION FOR SEQ ID NO:8:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CGCGAGATCT TCAAGCGTAG TCTGGGACGT CGTATGGGTA TATGCAGTGG CAGTCTTTGG       60

C                                                                       61

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCGCAGATCT GCCACCATGC TCCTGGTGTT GCT                                    33

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGCGAGATCT TCATATGCAG TGGCAGTCTT TGGC                                   34
```

POLYNUCLEOTIDES ENCODING PROSTATIC GROWTH FACTOR AND PROCESS FOR PRODUCING PROSTATIC GROWTH FACTOR POLYPEPTIDES

This application is entitled to the benefits of 35 U.S.C. §120 for priority based on PCT/US94/14578, filed Dec. 15, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a prostatic growth factor which is sometimes hereinafter referred to as "PGF".

This invention relates to a polynucleotide and polypeptide molecules which are structurally and functionally related to TGF-β. The transforming growth factor-beta family of peptide growth factors includes five members, termed TGF-β1 through TGF-β5, all of which form homo-dimers of approximately 25 kd. The TGF-β family belongs to a larger, extended super family of peptide signaling molecules that includes the Muellerian inhibiting substance (Cate, R. L. et al., Cell, 45:685–698 (1986)), decapentaplegic (Padgett, R. W. et al., Nature, 325:81–84 (1987)), bone morphogenic factors (Wozney, J. M. et al., Science, 242:1528–1534 (1988)), vg1 (Weeks, D. L., and Melton, D. A., Cell, 51:861–867 (1987)), activins (Vale, W. et al., Nature, 321:776–779 (1986)), and inhibins (Mason, A. J. et al., Nature, 318:659–663 (1985)). These factors are similar to TGF-β in overall structure, but share only approximately 25% amino acid identity with the TGF-β proteins and with each other. All of these molecules are thought to play an important roles in modulating growth, development and differentiation. The protein of the present invention, PGF, retains the seven cysteine residues conserved in the C-terminal, active domain of TGF-β.

TGF-β was originally described as a factor that induced normal rat kidney fibroblasts to proliferate in soft agar in the presence of epidermal growth factor (Roberts, A. B. et al., PNAS USA, 78:5339–5343 (1981)). TGF-β has subsequently been shown to exert a number of different effects in a variety of cells. For example, TGF-β can inhibit the differentiation of certain cells of mesodermal origin (Florini, J. R. et al., J. Biol. Chem., 261:1659–16513 (1986)), induced the differentiation of others (Seyedine, S. M. et al., PNAS USA, 82:2267–2271 (1985)), and potently inhibit proliferation of various types of epithelial cells, (Tucker, R. F., Science, 226:705–707 (1984)). This last activity has lead to the speculation that one important physiologic role for TGF-β is to maintain the repressed growth state of many types of cells. Accordingly, cells that lose the ability to respond to TGF-β are more likely to exhibit uncontrolled growth and to become tumorigenic. Indeed, the cells lack certain tumors such as retinoblastomas lack detectable TGF-β receptors at their cell surface and fail to respond to TGF-β, while their normal counterparts express self-surface receptors in their growth is potently inhibited by TGF-β (Kim Chi, A. et al., Science, 240:196–198 (1988)).

More specifically, TGF-β1 stimulates the anchorage-independent growth of normal rat kidney fibroblasts (Robert et al., PNAS USA, 78:5339–5343 (1981)). Since then it has been shown to be a multi-functional regulator of cell growth and differentiation (Sporn et al., Science, 233:532–534 (1986)) being capable of such diverse effects of inhibiting the growth of several human cancer cell lines (Roberts et al., PNAS-USA, 82:119–123 (1985)), mouse keratinocytes, (Coffey et al., Cancer RES., 48:1596–1602 (1988)), and T and B lymphocytes (Kehrl et al., J. Exp. Med., 163:1037–1050 (1986)). It also inhibits early hematopoietic progenitor cell proliferation (Goey et al., J. Immunol., 143:877–880 (1989)), stimulates the induction of differentiation of rat muscle mesenchymal cells and subsequent production of cartilage-specific macro molecules (Seyedine et al., J. Biol. Chem., 262:1946–1949 (1986)), causes increased synthesis and secretion of collagen (Ignotz et al., J. Biol. Chem., 261:4337–4345 (1986)), stimulates bone formation (Noda et al., Endocrinology, 124:2991–2995 (1989)), and accelerates the healing of incision wounds (Mustoe et al., Science, 237:1333–1335 (1987)).

Further, TGF-β1 stimulates formation of extracellular matrix molecules in the liver and lung. When levels of TGF-β1 are higher than normal, formation of fiber occurs in the extracellular matrix of the liver and lung which can be fatal. High levels of TGF-β1 occur due to chemotherapy and bone marrow transplant as an attempt to treat cancers, eg. breast cancer.

A second protein termed TGF-β2 was isolated from several sources including demineralized bone, a human prostatic adenocarcinoma cell line (Ikeda et al., Bio. Chem., 26:2406–2410 (1987)). TGF-β2 shared several functional similarities with TGF-β1. These proteins are now known to be members of a family of related growth modulatory proteins including TGF-β3 (Ten-Dijke et al., PNAS-USA, 85:471–4719 (1988)), Muellerian inhibitory substance and the inhibins. Due to amino acid sequence homology, it is thought that the PGF polypeptide of the present invention is also a member of this family of related growth modulatory proteins. However, to date, this polypeptide has only been found by the inventors to be present in the prostate.

In accordance with one aspect of the present invention, there is provided a novel mature polypeptide which is PGF, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding human PGF, including mRNAs, DNAs, cDNAs, genomic DNAs as well as analogs and biologically active and diagnostically or therapeutically useful fragments and derivatives thereof.

In accordance with yet a further aspect of the present invention, there is provided a process for producing such polypeptide by recombinant techniques comprising culturing recombinant prokaryotic and/or eukaryotic host cells, containing a human PGF nucleic acid sequence, under conditions promoting expression of said protein and subsequent recovery of said protein..

In accordance with yet a further aspect of the present invention, there is provided a process for utilizing such polypeptide, or polynucleotide encoding such polypeptide for therapeutic purposes, for example, to inhibit prostate cancer, stimulate tissue regeneration and to promote wound healing.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of PGF-dependent tumors.

In accordance with yet a further aspect of the present invention, there are also provided nucleic acid probes comprising nucleic acid molecules of sufficient length to specifically hybridize to human PGF sequences.

In accordance with still another aspect of the present invention, there are provided diagnostic assays for detecting diseases related to the under-expression and over-expression of the PGF polypeptide and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 depicts the cDNA sequence (SEQ ID NO:1) and corresponding deduced amino acid sequence (SEQ ID NO:2) of PGF. The standard one-letter abbreviations for amino acids are used. Sequencing was performed using a 373 Automated DNA sequencer (Applied Biosystems, Inc.). Sequencing accuracy is predicted to be greater than 97% accurate.

FIG. 2 is an illustration of comparative amino acid homology between the amino acid sequence of PGF and of two other proteins. The sequences are represented by one-letter amino acid codes and are show in relative alignment to one another. The first line is the relevant portion of PGF (SEQ ID NO:2) as compared to lines two and three, OP-1 (human osteogenic protein, SEQ ID NO:3) and Vg-1 (*X. laevis* vegetal hemisphere Vg-1 protein precursor, SEQ ID NO:4), respectively. Although gaps may be shown in the amino acid sequences in the comparative illustration of FIG. 2, for convenience SEQ ID NOS:3 and 4 are placed in the sequence listing as continuous sequences.

In accordance with an aspect of the present invention, there is provided an isolated nucleic acid (polynucleotide) which encodes for the mature polypeptide having the deduced amino acid sequence of FIG. 1 or for the mature polypeptide encoded by the cDNA of the clone deposited as ATCC Deposit 75902 on Sep. 28, 1994.

The ATCC number referred to above is directed to a biological deposit with the ATCC, 10801 University Boulevard, Manassas, Va. 20110-2209. Since the strain referred to is being maintained under the terms of the Budapest Treaty, it will be made available to a patent office signatory to the Budapest Treaty.

A polynucleotide encoding a polypeptide of the present invention may be obtained from human fetal spleen, prostate and 6 week old embryo. The polynucleotide of this invention was discovered in a cDNA library derived from human prostate. It is structurally related to the TGF-β family. It contains an open reading frame encoding a protein of approximately 276 amino acid residues of which approximately the first 15 amino acids residues are the putative leader sequence such that the mature protein comprises 261 amino acids. The protein exhibits the highest degree of homology to human osteogenic protein 1 (OP-1) with 33% identity and 57% similarity over a 45 amino acid stretch. The polypeptide contains the seven conserved cysteine amino acids characteristic of the TGF-β family members C-terminal domain.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same mature polypeptide as the DNA of FIG. 1 or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the PGF genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, *Salmonella typhimurium;* fungal cells, such as yeast; insect cells such as Drosophila S2 and Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially-available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The PGF polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

PGF polypeptides may be used to reduce or inhibit prostate cancer cell growth. PGF may affect a variety of cells in different ways, inducing growth in certain cells while inhibiting growth in others. Cancer cell lines, including prostatic adenocarcinoma, may be treated with PGF.

PGF may also be employed to promote wound healing, such as first, second and third degree burns, epidermal and internal incisions and those incisions resulting from cosmetic surgery. PGF may also be employed to stimulate tissue regeneration.

The polynucleotides and polypeptides of the present invention may be employed as research reagents and materials for discovery of treatments and diagnostics for human disease.

Fragments of the full length PGF gene may be used as a hybridization probe for a cDNA library to isolate the full length PGF gene and to isolate other genes which have a high sequence similarity to the PGF gene or similar biological activity. Probes of this type can be, for example, between 20 and 2000 base pairs. Preferably, however, the probes have between 30 and 50 bases. The probe may also be used to identify a cDNA clone corresponding to a full length transcript and a genomic clone or clones that contain the complete PGF gene including regulatory and promotor regions, exons, and introns. An example of a screen comprises isolating the coding region of the PGF gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides a method for identification of the receptor for PGF. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to PGF, and a cDNA library created from this RNA is divided into pools and used to transfect COS cells or other cells that are not responsive to PGF. Transfected cells which are grown on glass slides are exposed to labeled PGF. PGF can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled PGF can be photoaffinity linked with cell membrane or extract preparations that express the receptor molecule. Cross-linked material is resolved by PAGE and exposed to X-ray film. The labeled complex containing the PGF-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention is also related to a method of screening compounds to identify those which mimic PGF (agonists) or prevent the effect of PGF. An example of such a method takes advantage of the ability of PGF to significantly stimulate the proliferation of human endothelial cells in the presence of the comitogen Con A. Endothelial cells are obtained and cultured in 96-well flat-bottomed culture plates (Costar, Cambridge, Mass.) in RPM1 1640 supplemented with 10% heat-inactivated fetal bovine serum (Hyclone Labs, Logan, Utah), 1% L-glutamine, 100 U/ml penicillin, 100 $\mu$g/ml streptomycin, 0.1% gentamicin (Gibco Life Technologies, Grand Island, N.Y.) in the presence of 2 $\mu$g/ml of Con-A (Calbiochem, La Jolla, Calif.). Con-A, and the compound to be screened are added to a final volume of 0.2 ml. After 60 h at 37° C., cultures are pulsed with 1 $\mu$Ci of $^3$[H]thymidine (5 Ci/mmol; 1 Ci=37 BGq; NEN) for 12–18 h and harvested onto glass fiber filters (PhD; Cambridge Technology, Watertown, Mass.). Mean $^3$[H]thymidine incorporation (cpm) of triplicate cultures is determined using a liquid scintillation counter (Beckman Instruments, Irvine, Calif.). Significant $^3$[H]thymidine incorporation indicates stimulation of endothelial cell proliferation.

Alternatively, the response of a known second messenger system following interaction of PGF and receptor would be measured and compared in the presence or absence of the compound. Such second messenger systems include but are not limited to, CAMP guanylate cyclase, ion channels or phosphoinositide hydrolysis.

To assay for antagonists, the assay described above is performed, however, in this assay PGF is added along with the compound to be screened and the ability of the compound to inhibit $^3$[H]thymidine incorporation in the presence of PGF, indicates that the compound is an antagonist to PGF. Alternatively, PGF antagonists may be detected by combining PGF and a potential antagonist with membrane-bound PGF receptors or recombinant receptors under appropriate conditions for a competitive inhibition assay. PGF can be labeled, such as by radioactivity, such that the number of PGF molecules bound to the receptor can determine the effectiveness of the potential antagonist.

Alternatively, a mammalian cell or membrane preparation expressing the PGF receptor is incubated with labeled PGF in the presence of the compound. The ability of the compound to enhance or block this interaction could then be measured.

Examples of potential PGF antagonists include an antibody, or in some cases, an oligonucleotide, which binds to the polypeptide. Alternatively, a potential antagonist may be a closely related protein, for example a mutated form of the protein, which binds to the receptor sites, however, they are inactive forms of the polypeptide and thereby prevent the action of PGF since receptor sites are occupied.

Another potential PGF antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of PGF. The antisense RNA oligonucleotide hybridizes to the mRNA in vivo and blocks translation of the mRNA molecule into PGF polypeptide (Antisense-Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of PGF.

Potential PGF antagonists include a small molecule which binds to and occupies the active site of the polypeptide thereby making it inaccessible to substrate such that normal biological activity is prevented. Examples of small molecules include but are not limited to small peptides or peptide-like molecules and non-peptide molecules.

The antagonists may be employed to treat PGF-dependent prostate cancer and benign prostatic hyperplasia (BPH). The antagonists may be employed in a composition with a pharmaceutically acceptable carrier, e.g., as hereinafter described.

The PGF polypeptides and agonists and antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The PGF polypeptides, and agonists and antagonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

This invention is also related to the use of the PGF gene as a diagnostic. Detection of a mutated form of PGF will allow a diagnosis of a disease or a susceptibility to a disease which results from underexpression of PGF.

Individuals carrying mutations in the human PGF gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding PGF can be used to identify and analyze PGF mutations. For example, deletions and insertions can be detected by a change in size of the amplified product in comparison to the normal genotype. Point mutations can be identified by hybridizing amplified DNA to radiolabeled PGF RNA or alternatively, radiolabeled PGF antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of PGF protein in various tissues since an over-expression of the proteins compared to normal control tissue samples allows early detection of prostate cancer or benign prostatic hyperplasia. Assays used to detect levels of PGF protein in a sample derived from a host are well-known to those of skill in the art and include radioimmunoassays, competitive-binding assays, Western Blot analysis and preferably an ELISA assay.

An Elisa assay initially comprises preparing an antibody specific to the PGF antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any PGF proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to PGF. Unattached reporter antibody is then washed out. Peroxidase substrates are then added to the dish and the amount of color developed in a given time period is a measurement of the amount of PGF protein present in a given volume of patient sample when compared against a standard curve.

A competition assay may be employed wherein antibodies specific to PGF is attached to a solid support and labeled PGF and a sample derived from the host are passed over the solid support and the amount of label detected attached to the solid support can be correlated to a quantity of PGF in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the express sequence tag (EST) was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of PGF

The DNA sequence encoding PGF, ATCC #75902, is initially amplified using PCR oligonucleotide primers corresponding to the 5' and 3' termini. Additional nucleotides corresponding to PGF are added to the 5 ' and 3' sequences, respectively. The 5' oligonucleotide primer has the sequence 5' CGCGCGAAGCTTATGCTCCTGGTGTTGCTGGTG 3' (SEQ ID NO:5) contains a HindIII restriction enzyme site followed by 21 nucleotides of PGF coding sequence starting from the first amino acid. The 3' sequence 5' GCGCGCTCTAGATCATATGCAGTGGCAGTCTTT 3' (SEQ ID NO:6) contains complementary sequences to an XbaI site and is followed by 21 nucleotides of PGF. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform E. coli strain m15/pREP4 (Qiagen) by the procedure described in Sambrook, J. et al., Molecular Cloning: A Laboratory Manual, Cold Spring Laboratory Press, (1989). M15/pREP4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized PGF is purified from this solution by chromatography on a Nickel-Chelate column under conditions that allow for tight binding by proteins containing the 6-His tag (Hochuli, E. et al., J. Chromatography 411:177–184 (1984)). PGF is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Expression of Recombinant PGF in COS cells

The expression of plasmid, PGF HA is derived from a vector N11 containing: 1) SV40 origin of replication, 2) ampicillin resistance gene, 3) E. coli replication origin, 4) CMV promoter followed by a polylinker region, a rat preproinsulin 3' intron and polyadenylation site. A DNA fragment encoding the entire PGF precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding PGF, ATCC #75902, was constructed by PCR using two primers: the 5' primer 5' GCGC AGATCTGCCACCATGCTCCTGGTGTTGCTGGTGCTG 3' (SEQ ID NO:7) contains a Bgl II site followed by 24 nucleotides of PGF coding sequence starting from the initiation codon; the 3' sequence 5' CGCGAGATCT-TCAAGCGTAGTCTGGGACGTCGTATGGG-TATATGCAGTGGCAGTCTTTGGC 3' (SEQ ID NO:8) contains complementary sequences to a Bgl II site, translation stop codon, HA tag and the last 21 nucleotides of the PGF coding sequence (not including the stop codon). Therefore, the PCR product contains a Bgl II site, PGF coding sequence followed by HA tag fused in frame, a translation termination stop codon next to the HA tag, and an Bgl II site. The PCR amplified DNA fragment and the vector, N11 were digested with Bgl II restriction enzyme and ligated. The ligation mixture was transformed into E. coli strain DH5α (Stratagene Cloning Systems, La Jolla, Calif.) the transformed culture was plated on ampicillin media plates and resistant colonies were selected. Plasmid DNA was isolated from transformants and examined by restriction analysis for the presence of the correct fragment. For expression of the recombinant PGF, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the PGF HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Expression Pattern of PGF in Human Tissue

Northern blot analysis was carried out to examine the levels of expression of PGF in human tissues. Total cellular RNA samples were isolated with RNAzol™ B system (Biotecx Laboratories, Inc. 6023 South Loop East, Houston, Tex. 77033). About 10 μg of total RNA isolated from each human tissue specified was separated on 1% agarose gel and blotted onto a nylon filter (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column (5 Prime-3 Prime, Inc. Boulder, Colo. 80303). The filter was then hybridized with radioactive labeled full length PGF gene at 1,000,000 cpm/ml in 0.5 M NaPO$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for PGF is abundant in the prostate.

EXAMPLE 4

Expression of Recombinant PGF in CHO Cells

The vector pN346 is used for the expression of the PGF protein. Plasmid pN346 is a derivative of the plasmid pSV2-dhfr [ATCC Accession No. 37146]. Both plasmids contain the mouse dhfr gene under control of the SV40 early promoter. Chinese hamster ovary—or other cells lacking dihydrofolate activity that are transfected with these plasmids can be selected by growing the cells in a selective medium (alpha minus MEM, Lift Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the dhfr gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pN346 contains for the expression of the gene of interest a strong promoter of the long terminal repeat (LTR) of the Rouse Sarcoma Virus (Cullen, et al., Molecular and Cellular Biology, March 1985, 438–447) plus a fragment isolated from the enhancer of the immediate early gene of human cytomegalovirus (C4V) (Boshart et al., Cell 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g. G418 plus methotrexate.

The plasmid pN346 was digested with the restriction enzyme BamHI and then dephosphorylated using calf intestinal phosphatase by procedures known in the art. The vector was then isolated from a 1% agarose gel.

The DNA sequence encoding PGF, ATCC #75902, was amplified using PCR oligonucleotide primers corresponding to the 5' and 3' sequences of the gene:

The 5 ' primer has the sequence GCGCAGATCTGC-CACC<u>ATG</u>CTCCTGGTGTTGCT (SEQ ID NO:9) and contains a BglII restriction enzyme site (in bold) followed by 17 nucleotides resembling an efficient signal for translation (Kozak, M., supra) plus the first 17 nucleotides of the gene (the initiation codon for translation "ATG" is underlined.).

The 3' primer has the sequence 5' CGCGAGATCT-TCATATGCAGTGGCAGTCTTTGGC 3' (SEQ ID NO:10) and contains the cleavage site for the restriction endonuclease BglII (in bold) and 20 nucleotides complementary to the 3' non-translated sequence of the gene.

The amplified fragments were isolated from a 1% agarose gel as described above and then digested with the endonuclease BglII and then purified again on a 1% agarose gel.

The isolated fragment and the dephosphorylated vector were then ligated with T4 DNA ligase. *E. coli* HB101 cells were then transformed and bacteria identified that contained the plasmid pN346 inserted in the correct orientation using the restriction enzymes BamHI. The sequence of the inserted gene was confirmed by DNA sequencing.

Transfection of CHO-dhfr-cells

Chinese hamster ovary cells lacking an active DHFR enzyme were used for transfection. 5 µg of the expression plasmid N346 were cotransfected with 0.5 µg of the plasmid pSvneo using the lipofectin method (Felgner et al., supra). The plasmid pSV2-neo contains a dominant selectable marker, the gene neo from Tn5 encoding an enzyme that confers resistance to a group of antibiotics including G418. The cells were seeded in alpha minus MEM supplemented with 1 mg/ml G418. After 2 days, the cells were trypsinized and seeded in hybridoma cloning plates (Greiner, Germany) and cultivated from 10–14 days. After this period, single clones were trypsinized and then seeded in 6-well petri dishes using different concentrations of methotrexate (25, 50 nm, 100 nm, 200 nm, 400 nm). Clones growing at the highest concentrations of methotrexate were then transferred to new 6-well plates containing even higher concentrations of methotrexate (500 nM, 1 µM, 2 µM, 5 µM). The same procedure was repeated until clones grew at a concentration of 100 µM.

The expression of the desired gene product was analyzed by Western blot analysis and SDS-PAGE.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide member selected from the group consisting of:

(a) a polynucleotide encoding a polypeptide comprising amino acids 16 to 295 of SEQ ID NO:2; and (b) the complement of (a).

2. The isolated polynucleotide of claim 1 wherein said member is (a).

3. A method of making a recombinant vector comprising inserting the isolated polynucleotide of claim 2 into a vector.

4. A recombinant vector comprising the polynucleotide of claim 2.

5. The recombinant vector of claim 4 wherein said polynucleotide is operatively associated with a heterologous regulatory sequence that controls gene expression.

6. A recombinant host cell comprising the polynucleotide of claim 2.

7. A process for producing a polypeptide comprising:
   culturing a recombinant cell containing the polynucleotide of claim 2 under conditions suitable to produce the polypeptide encoded by said polynucleotide and isolating said polypeptide.

8. The isolated polynucleotide of claim 1 wherein said member is (a) and the polypeptide comprises amino acids 1 to 295 of SEQ ID NO:2.

9. The isolated polynucleotide of claim 1 wherein said member is (b).

10. The isolated polynucleotide of claim 1 wherein the polynucleotide is DNA.

11. The isolated polynucleotide of claim 1 wherein said polynucleotide is RNA.

12. The isolated polynucleotide of claim 1 comprising nucleotides 67 to 948 of SEQ ID NO:1.

13. The isolated polynucleotide of claim 1 comprising nucleotides 64 to 951 of SEQ ID NO:1.

14. The isolated polynucleotide of claim 1 comprising the polynucleotide having a polynucleotide sequence of SEQ ID NO:1.

15. The isolated polynucleotide of claim 1 comprising nucleotides 112 to 948 of SEQ ID NO:1.

16. The isolated polynucleotide of claim 1 further comprising a heterologous polynucleotide.

17. The isolated polynucleotide of claim 16 wherein said heterologous polynucleotide encodes a heterologous polypeptide.

18. An isolated polynucleotide comprising a polynucleotide member selected from the group consisting of:
   (a) a polynucleotide encoding the same mature polypeptide encoded by the human cDNA in ATCC Deposit No. 75902; and
   (b) the complement of (a).

19. The isolated polynucleotide of claim 18, wherein the member is (a).

20. A process for producing a polypeptide comprising:
   culturing a recombinant cell containing the polynucleotide of claim 19 under conditions suitable to produce the polypeptide encoded by said polynucleotide and
   isolating said polypeptide.

21. The isolated polynucleotide of claim 18 wherein the member is (b).

22. The isolated polynucleotide of claim 18 wherein the polynucleotide is DNA.

23. The isolated polynucleotide of claim 18 wherein said polynucleotide is RNA.

24. A method of making a recombinant vector comprising inserting the isolated polynucleotide of claim 18 into a vector.

25. A recombinant vector comprising the polynucleotide of claim 18.

26. The recombinant vector of claim 25 wherein said polynucleotide is operatively associated with a heterologous regulatory sequence that controls gene expression.

27. A recombinant host cell comprising the polynucleotide of claim 18.

28. The isolated polynucleotide of claim 18 further comprising a heterologous polynucleotide.

29. The isolated polynucleotide of claim 28 wherein said heterologous polynucleotide encodes a heterologous polypeptide.

* * * * *